United States Patent [19]

Nishikawa et al.

[11] Patent Number: 4,551,556

[45] Date of Patent: Nov. 5, 1985

[54] PROCESS FOR PRODUCING CARBONYL COMPOUNDS

[75] Inventors: Eiichiro Nishikawa; Masuo Shinya, both of Saitama; Kayako Ueda, Tokyo; Katsumi Kaneko, Saitama, all of Japan

[73] Assignee: Toa Nenryo Kogyo Kabushiki Kaisha, Tokyo, Japan

[21] Appl. No.: 601,544

[22] Filed: Apr. 18, 1984

[30] Foreign Application Priority Data

May 2, 1983 [JP] Japan ................................. 58-76173

[51] Int. Cl.$^4$ ............................................. C07C 45/00
[52] U.S. Cl. .................................. 568/403; 568/487; 568/489
[58] Field of Search ................ 568/403, 487, 489, 361

[56] References Cited

U.S. PATENT DOCUMENTS

| | | |
|---|---|---|
| 1,827,317 | 10/1931 | Jaeger .................................. 568/361 |
| 2,083,877 | 6/1937 | Steck et al. ......................... 568/489 |
| 2,701,264 | 2/1955 | Deahl et al. ........................ 568/403 |
| 2,835,706 | 5/1958 | Cordes ................................ 568/403 |
| 3,778,477 | 12/1973 | Mueller et al. ..................... 568/403 |
| 3,836,553 | 9/1974 | Fenton ................................ 568/361 |
| 3,884,981 | 5/1975 | Kiff ..................................... 568/403 |
| 4,075,128 | 2/1978 | Zak ..................................... 568/403 |

FOREIGN PATENT DOCUMENTS 849135  8/1958  United Kingdom .

OTHER PUBLICATIONS

Inorg. Chem., 16 (1), 137 (1977).
Gazz. Chim., Ital., 91, 479 (1961).

*Primary Examiner*—James H. Reamer
*Attorney, Agent, or Firm*—Jack B. Murray, Jr.

[57] ABSTRACT

The invention relates to a process of producing a carbonyl compound by dehydrogenating a linear aliphatic alcohol of 1 to 6 carbon atoms in the gas phase in the presence of a solid catalyst comprising a ruthenium catalyst supported on a carrier such as zinc oxide or magnesium oxide.

8 Claims, No Drawings

PROCESS FOR PRODUCING CARBONYL COMPOUNDS

FIELD OF THE INVENTION

The present invention relates to a process for producing a carbonyl compound by dehydrogenating an aliphatic alcohol. More particularly, it relates to a process for dehydrogenating an aliphatic alcohol in the gas phase using a specific solid catalyst, thereby producing a corresponding aldehyde or ketone.

BACKGROUND OF THE INVENTION

Heretofore, there have been industrial processes for producing acetone by dehydrogenating isopropanol and for producing methyl ethyl ketone (MEK) by dehydrogenating sec-butanol in the presence of a solid catalyst. The solid catalyst for such processes is usually zinc oxide or a copper-zinc alloy, and they are used at high temperatures above 400° C. because they are low in activity at low temperatures.

It is reported that the dehydrogenation of alcohols at low temperatures is effectively catalyzed by a copper-complex oxide such as $CuO-ZnO$, $CuO-Cr_2O_3$, and $CuO-coO-Cr_2O_3$. However, these catalysts have a drawback in common in that they lose activity very soon and need frequent regeneration. This drawback places them under a practical disadvantage.

Recently an attempt has been made to dehydrogenate an alcohol in the homogeneous liquid phase by using a complex compound of ruthenium or osmium as a catalyst. [Inorg. Chem., 16(1), 137 (1977)] This process, however, has not yet reached the level of practical use.

There is known a process for producing n-decanal by dehydrogenating n-decanol using a ruthenium catalyst supported on alumina. [Gazz. Chim. Ital., 91, 479 (1961)] It is reported that this process is such that the reaction does not proceed when there is no oxygen in the reaction system.

There is also known a process for producing an alicyclic ketone by dehydrogenating an alicyclic alcohol using a ruthenium catalyst supported on a carrier such as carbon or metal oxide although only the former is exemplified (British Pat. No. 849,135). This process has the disadvantage of using essentially carbon as a carrier. The catalyst is easily deactivated by the carrier. Moreover, the catalyst requires a reaction temperature higher than 300° C., at which dehydration and other side reactions take place. For these reasons, this process has not been put to practical use.

The object of the invention is to provide a catalyst that exhibits high catalytic activity at low temperatures and maintains activity for a long time in the process for producing a carbonyl compound by dehydrogenating a lower aliphatic alcohol of 1 to 6 carbon atoms. Applicants found that the object can be achieved by a ruthenium catalyst supported on a carrier.

SUMMARY OF THE INVENTION

The gist of this invention resides in a process for producing a carbonyl compound which comprises dehydrogenating a linear alphatic alcohol of carbon number 1 to 6 in gas phase in the presence of a ruthenium catalyst supported on a carrier.

DETAILED DESCRIPTION

Carrier

The carrier used in this invention includes for example, zinc oxide, magnesium oxide, calcium oxide, barium oxide, sodium carbonate, potassium carbonate, calcium carbonate, barium carbonate, strontium carbonate, magnesium carbonate, alumina, silica alumina, silica, activated carbon, zeolite, and titania. Preferred among them are basic oxides such as zinc oxide, magnesium oxide, calcium oxide, and barium oxide.

If these basic oxides are of high purity, they can be used without any problem; in the case of commerical products, however, they should preferably be incorporated with an alkaline substance such as potassium carbonate and sodium carbonate because they often contain a small amount of acidic sites derived from impurities.

These carriers may be used individually or in combination with one another.

Preparation of catalyst

The catalyst used in this invention is ruthenium supported on the above-mentioned carrier. The supporting can be accomplished by steeping a carrier in a solution of ruthenium compound in water or organic solvent, followed by evaporation to dryness; or by steeping a carrier in a solution of ruthenium compound in water or organic solvent, and removing the solvent by filtration or decantation, followed by drying or by washing and calcination.

The ruthenium compound to be supported includes, for example, ruthenium chloride, ruthenium bromide, ruthenium iodide, ruthenium nitrate, ammonium chlororuthenate, ammonium bromoruthenate, ammonium iodoruthenate, sodium ruthenate, potassium ruthenate, ruthenium hydroxide, ruthenium oxide, and ruthenium carbonyl.

The quantity of ruthenium to be supported is suitably 0.01 to 10 wt. %, preferably 0.1 to 5 wt. %.

Before use for the dehydrogenation reaction, the catalyst should preferably be treated with hydrogen or a reducing organic compound such as hydrazine, formalin, or methanol at room temperature to 500° C.

Alcohol

The alcohol used as a feedstock in the process of this invention is a linear aliphatic alcohol of carbon number 1 to 6. Examples of such an alcohol include methanol, ethanol, n-propanol, n-butanol, 2-methyl-propanol, n-pentanol, 3-methylbutanol, 2-methylbutanol, n-hexanol, 4-methylpentanol, 2-methylpentanol, and other primary alcohols; and 2-propanol, 2-butanol, 3-pentanol, 2-pentanol, 3-hexanol, 2-hexanol, and other secondary alcohols.

When dehydrogenated according to the process of this invention, the primary alcohols form their corresponding aldehydes and the secondary alcohols form their corresponding ketones.

Method of dehydrogenation

The dehydrogenation is accomplished by bringing the alcohol into contact with the catalyst. The catalyst is placed in a fixed bed or fluidized bed; and the alcohol is supplied continuously or batchwise.

The reaction conditions are not specifically limited. The reaction pressure should preferably be reduced pressure or normal pressure; but reaction under pressure up to about 30 kg/cm² is permissible. The reaction temperature should be 150° to 400° C., which is high enough to keep the reaction system in the gaseous state, and preferably is 200° to 250° C. The alcohol in liquid form should be supplied at a rate (LHSV) of 0.1 to 100 hr$^{-1}$, preferably 0.5 to 20 hr$^{-1}$.

If the catalyst of this invention is used, it is possible to produce a desired carbonyl compound at a sufficiently high conversion rate and selectivity at a low temperature without using a heating furnace. Moreover, the catalyst maintains its high catalytic activity for a long time. The catalyst is particularly suitable for converting a secondary alcohol among the above-mentioned alcohols into its corresponding ketone on an industrial scale.

The invention is described in more detail with reference to the following non-limiting examples and referential examples, in which "%" means "wt %", unless otherwise noted.

EXAMPLE 1

Zinc oxide (20 to 40 mesh) was steeped in a ruthenium chloride solution prepared by dissolving a predetermined quantity of ruthenium chloride in acetone. (The zinc oxide was prepared by pulverizing the commerical one available as a catalyst for alcohol dehydrogenation. It contained 3.3% of sodium carbonate.) After standing for 1 hour, the solution was evaporated to dryness, followed by drying in an oven at 120° C. for 12 hours. The resulting product was reduced with nitrogen saturated (at room temperature) with methanol at 200° C. for 1 hour and then at 400° C. for 1 hour. Thus there was obtained a catalyst containing 1% of ruthenium.

2.5 cc of this catalyst was diluted with 7.5 cc of quartz chips and the diluted catalyst was introduced into a stainless steel reactor tube, 18 mm in inside diameter. 2-Butanol was passed through the reactor tube for dehydrogenation under the conditions and with the results shown in Table 1.

COMPARATIVE EXAMPLE 1

Dehydrogenation of alcohol was carried out in the same way as in Example 1, except that the zinc oxide powder used at the carrier was used as a catalyst as such. The results are shown in Table 1.

TABLE 1

| Example No. | Catalyst | Reaction conditions* | | MEK yield (mol %)** | | |
|---|---|---|---|---|---|---|
| | | Temp. (°C.) | LHSV (hr$^{-1}$) | After 2 hr | After 30 hr | After 150 hr |
| Example 1 | Ru/ZnO | 250 | 8 | 23 | 23 | 23 |
| Compar. Example 1 | ZnO | 250 | 2 | 2 | 2 | 13 |
| Compar. Example 2 | CuO—ZnO | 200 | 40 | 24 | 4 | — |
| Compar. Example 3 | CuO/diatomaceous earth | 200 | 40 | 25 | 6 | — |
| Compar. Example 3 | CuO/diatomaceous earth | 250 | 40 | 43 | 14 | — |

Note:
*Reaction pressure was 10 kg/cm²G in all the cases.
**Selectivity to MEK (methyl ethyl ketone) was higher than 99 mol %.

COMPARATIVE EXAMPLE 2

Dehydrogenation of alcohol was carried out in the same way as in Example 1, except that the catalyst was replaced by a commerical copper oxide-zinc oxide catalyst for alcohol dehydrogenation (CuO: 50%, ZnO: 45%, specific surface area: 38.0 m²/g) which had been crushed to 20 to 40 mesh prior to use. The results are shown in Table 1.

COMPARATIVE EXAMPLE 3

Dehydorgenation of alcohol was carried out in the same way as in Example 1, except that the catalyst was replaced by a commerical copper oxide catalyst for alcohol dehydrogenation (CuO: 70%/diatomaceous earth, specific surface area: 171 m²/g) which had been crushed to 20 to 40 mesh prior to use. The results are shown in Table 1.

As Table 1 shows, zinc oxide exhibits very low activity when used alone and a copper oxide catalyst becomes considerably deactivated with time, whereas the catalyst of this invention is superior in activity and keeps up the high activity for a long time.

EXAMPLE 2

A catalyst containing 2% of ruthenium was prepared in the same way as in Example 1, except that the zinc oxide was replaced by commerical magnesium oxide (MgO: 98%, specific surface area: 15 m²/g) which had been crushed to 20 to 40 mesh prior to use.

With this catalyst, the dehydrogenation reaction was carried out in the same way as in Example 1. The results are shown in Table 2.

EXAMPLE 3

Magnesium oxide powder (20 to 40 mesh) as used in Example 2 was steeped in an aqueous solution of sodium carbonate prepared by dissolving a predetermined quantity of sodium carbonate in water. After standing for 1 hour, the solution was evaporated to dryness, followed by drying in an oven at 120° C. for 12 hours. The resulting product was then calcined in a muffle furnace at 400° C. for 1 hour. The resulting magnesium oxide containing 3.3% of sodium carbonate was used as a carrier. Thus a catalyst containing 2% of ruthenium was prepared in the same way as in Example 1.

With this catalyst, dehydrogenation of 2-butanol was carried out in the same way as in Example 1. The results are shown in Table 2.

TABLE 2

| Example No | Catalyst | Reaction temperature (°C.) | MEK yield (mol %) | MEK selectivity (mol %) |
|---|---|---|---|---|
| Example 2 | Ru/MgO | 250 | 19 | 97 |
| Example 3 | Ru/MgO—Na$_2$CO$_3$ | 250 | 21 | 99 |

Note:
Reaction pressure: 10 kg/cm²G, LHSV (hr$^{-1}$): 8, and reaction time: 100 hours.

EXAMPLE 4

Ruthenium (1%)-zinc oxide catalyst was prepared in the same way as in Example 1. without dilution with quartz chips, the catalyst (9 cc) was introduced into a stainless steel reactor tube, 20 mm in inside diameter. 2-Butanol was passed through the reactor tube at normal pressure and at an LHSV of 2 hr$^{-1}$. Table 3 shows the results obtained 2 hours after the start of the reaction.

COMPARATIVE EXAMPLE 4

A rhodium (1%)-zinc oxide catalyst was prepared in the same way as in Example 1, except that ruthenium chloride was replaced by rhodium chloride.

With this catalyst, dehydrogenation reaction was carried out in the same way as in Example 4. The results are shown in Table 3.

COMPARATIVE EXAMPLES 5 AND 6

An iridium (1%)-zinc oxide catalyst and a platinum (1%)-zinc oxide catalyst were prepared in the same way as in Example 1, except that ruthenium chloride was replaced by chloroiridinic acid and chloroplatinic acid, respectively.

With these catalysts, the dehydrogenation reaction was carried out in the same way as in Example 4. The results are shown in Table 3.

COMPARATIVE EXAMPLE 7

A palladium (1%)-zinc oxide catalyst was prepared in the same way as in Example 1, except that palladium chloride was dissolved in a mixture of concentrated hydrochloric acid (2 vol) and acetone (8 vol) instead of dissolving ruthenium chloride in acetone.

With this catalyst, the dehydrogenation reaction was carried out in the same way as in Example 4. The results are shown in Table 3.

COMPARATIVE EXAMPLE 8

A silver (1%)-zinc oxide catalyst was prepared in the same way as in Example 1, except that the acetone solution of ruthenium chloride was replaced by an aqueous solution of silver nitrate.

With this catalyst, the dehydrogenation reaction was carried out in the same way as in Example 4. The results are shown in Table 3.

TABLE 3

| Example No | Catalyst | Reaction temperature (°C.) | MEK yield (mol %) | MEK selectivity (mol %) |
| --- | --- | --- | --- | --- |
| Example 4 | Ru/ZnO | 200 | 20 | 100 |
|  |  | 250 | 72 | 100 |
| Comparative Example 4 | Rh/ZnO | 200 | 10 | 95 |
|  |  | 250 | 32 | 71 |
| Comparative Example 5 | Ir/ZnO | 200 | 2 | 67 |
|  |  | 250 | 8 | 37 |
| Comparative Example 6 | Pt/ZnO | 200 | 2 | 53 |
|  |  | 250 | 5 | 15 |
| Comparative Example 7 | Pd/ZnO | 200 | 1 | 10 |
|  |  | 250 | 6 | 26 |
| Comparative Example 8 | Ag/ZnO | 200 | 1 | 30 |
|  |  | 250 | 2 | 17 |

EXAMPLE 5

A catalyst containing 5% of ruthenium was produced in the same way as in Example 1, except that zinc oxide was replaced by activated carbon (20 to 40 mesh) which had been treated with 15% nitric acid under reflux for 6 hours.

With this catalyst, the dehydrogenation reaction was carried out in the same way as in Example 1 except as noted below. The results are shown in Table 4.

TABLE 4

| Reaction time | MEK Yield (mol %) | MEK selectivity (mol %) |
| --- | --- | --- |
| After 2 hr | 22 | 92 |
| After 30 hr | 15 | 95 |

Note:
Reaction temperature: 200° C.,
Reaction pressure: 10 kg/cm$^2$G, and LHSV (hr$^{-1}$): 40.

EXAMPLE 6

Ruthenium (1%)-magnesium oxide catalyst was prepared in the same way as in Example 2. Without dilution with quartz chips, the catalyst (9 cc) was placed in a stainless steel reactor tube, 20 mm in inside diameter. 2-Propanol was passed through the reactor tube under normal pressure, at 250° C., and at an LHSV of 2 hr$^{-1}$. Thirty hours after the start of the reaction, acetone was obtained in a yield of 88 mol %.

What is claimed is:

1. A process for producing a carbonyl compound which comprises dehydrogenating a linear aliphatic alcohol of 1 to 6 carbon atoms in the gas phase at a temperature of from 150° to 400° C. in the presence of a ruthenium catalyst supported on a carrier comprising a basic oxide selected from the group consisting of zinc oxide, magnesium oxide, calcium oxide and barium oxide.

2. The process according to claim 1 in which the alcohol is secondary butanol and the carbonyl compound produced in methyl ethyl ketone.

3. The process according to claim 1 or 2 in which the dehydrogenation is carried out at a temperature in the range of about 200° C. to 250° C.

4. The process according to claims 1 or 2 in which the carrier comprises zinc oxide or magnesium oxide with or without a minor amount of sodium carbonate.

5. The process according to claim 1 or 2 in which the ruthenium catalyst is reduced before use.

6. The process according to claim 1 or 2 in which the carrier supports 0.01 to 10 wt. % ruthenium.

7. A process for producing a carbonyl compound which comprises dehydrogenating a linear aliphatic alcohol of 1 to 6 carbon atoms in the gas phase at a temperature in the range of about 200° C. to 250° C. in the presence of a ruthenium catalyst supported on a carrier comprising zinc oxide or magnesium oxide.

8. The process according to claim 7 in which the alcohol is 2-propanol or 2-butanol and the carbonyl compound produced in acetone or methyl ethyl ketone, respectively.

* * * * *